United States Patent
Lentz et al.

(10) Patent No.: US 6,719,783 B2
(45) Date of Patent: Apr. 13, 2004

(54) PTFE VASCULAR GRAFT AND METHOD OF MANUFACTURE

(75) Inventors: David Lentz, LaJolla, CA (US); Jamie Henderson, Oakland, NJ (US); Edward Dormier, Rockaway, NJ (US); Richard Zdrahala, Eden Prairie, MN (US); Gary Loomis, Morristown, NJ (US); Ronald Rakos, Neshanic Station, NJ (US); Krzysztof Sowinski, Wallington, NJ (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/212,609

(22) Filed: Aug. 5, 2002

(65) Prior Publication Data

US 2003/0004559 A1 Jan. 2, 2003

Related U.S. Application Data

(60) Continuation of application No. 09/525,710, filed on Mar. 14, 2000, now Pat. No. 6,428,571, which is a continuation-in-part of application No. 09/008,265, filed on Jan. 16, 1998, now Pat. No. 6,036,724, which is a division of application No. 08/588,052, filed on Jan. 22, 1996, now Pat. No. 5,800,512.

(51) Int. Cl.$^7$ .................................................. A61F 2/06
(52) U.S. Cl. ....................................... 623/1.4; 623/1.49
(58) Field of Search ............................. 623/1.15, 1.27, 623/1.39, 1.4, 1.49

(56) References Cited

U.S. PATENT DOCUMENTS

| | | |
|---|---|---|
| 3,953,566 A | 4/1976 | Gore |
| 4,082,893 A | 4/1978 | Okita |
| 4,177,334 A | 12/1979 | Okita |

(List continued on next page.)

FOREIGN PATENT DOCUMENTS

| | | |
|---|---|---|
| EP | 716 836 | 6/1996 |
| EP | 775 472 | 5/1997 |
| JP | 3-349850 | 12/1991 |
| JP | 3-352338 | 12/1991 |
| JP | 3-359922 | 12/1991 |
| JP | 4-28337 | 2/1992 |
| JP | 4-73847 | 3/1992 |
| JP | 4-280512 | 9/1992 |
| JP | 4-303034 | 12/1992 |
| JP | 6-343688 | 12/1994 |
| JP | 5-321443 | 1/1995 |
| JP | 5-243819 | 3/1995 |
| WO | WO 95/05132 | 2/1995 |
| WO | WO 95/05277 | 2/1995 |
| WO | WO 95/05555 | 2/1995 |
| WO | WO 95/24304 | 9/1995 |
| WO | WO 96/28115 | 9/1996 |
| WO | WO 98/00090 | 1/1998 |

*Primary Examiner*—David H. Willse
*Assistant Examiner*—Suzette J. Jackson
(74) *Attorney, Agent, or Firm*—Hoffmann & Baron, LLP

(57) ABSTRACT

An implantable microporous ePTFE tubular vascular graft exhibits long term patency, superior radial tensile strength and suture hole elongation resistance. The graft includes a first ePTFE tube and a second ePTFE tube circumferentially disposed over the first tube. The first ePTFE tube exhibits a porosity sufficient to promote cell endothelization, tissue ingrowth and healing. The second ePTFE tube exhibits enhanced radial strength in excess of the radial tensile strength of the first tube.

25 Claims, 3 Drawing Sheets

U.S. PATENT DOCUMENTS

| | | |
|---|---|---|
| 4,250,138 A | 2/1981 | Okita |
| 4,304,010 A | 12/1981 | Mano |
| 4,385,093 A | 5/1983 | Hubis |
| RE31,618 E | 7/1984 | Mano et al. |
| 4,478,665 A | 10/1984 | Hubis |
| 4,478,898 A | 10/1984 | Kato |
| 4,482,516 A | 11/1984 | Bowman et al. |
| 4,576,608 A | 3/1986 | Homsy |
| 4,598,011 A | 7/1986 | Bowman |
| 4,619,641 A * | 10/1986 | Schanzer ................. 604/8 |
| 4,743,480 A | 5/1988 | Campbell et al. |
| 4,816,339 A | 3/1989 | Tu et al. |
| 4,857,069 A | 8/1989 | Kira |
| 4,877,661 A | 10/1989 | House et al. |
| 4,925,710 A | 5/1990 | Buck et al. |
| 4,955,899 A | 9/1990 | Della Corna et al. |
| 4,973,609 A | 11/1990 | Browne |
| 5,024,671 A | 6/1991 | Tu et al. |
| 5,026,513 A | 6/1991 | House et al. |
| 5,061,276 A | 10/1991 | Tu et al. |
| 5,116,360 A | 5/1992 | Pinchuk et al. |
| 5,123,917 A | 6/1992 | Lee |
| 5,152,782 A | 10/1992 | Kowligi et al. |
| 5,154,866 A | 10/1992 | Honda et al. |
| 5,192,310 A * | 3/1993 | Herweck et al. ........... 623/1.27 |
| 5,282,824 A | 2/1994 | Gianturco |
| 5,308,664 A | 5/1994 | House et al. |
| 5,354,329 A | 10/1994 | Whalen |
| 5,358,678 A | 10/1994 | Nakamura et al. |
| 5,370,681 A * | 12/1994 | Herweck et al. ........... 623/1.27 |
| 5,374,473 A | 12/1994 | Knox et al. |
| 5,389,106 A | 2/1995 | Tower |
| 5,433,909 A | 7/1995 | Martakos et al. |
| 5,437,900 A | 8/1995 | Kuzowski |
| 5,453,235 A | 9/1995 | Calcote et al. |
| 5,462,781 A | 10/1995 | Zukowski |
| 5,466,509 A | 11/1995 | Kowligi et al. |
| 5,507,771 A | 4/1996 | Gianturco |
| 5,562,697 A | 10/1996 | Christiansen |
| 5,562,728 A | 10/1996 | Lazarus et al. |
| 5,584,876 A | 12/1996 | Bruchman et al. |
| 5,591,195 A | 1/1997 | Taheri et al. |
| 5,620,763 A | 4/1997 | House et al. |
| 5,653,697 A | 8/1997 | Quiachon et al. |
| 5,674,241 A | 10/1997 | Bley et al. |
| 5,700,285 A | 12/1997 | Myers et al. |
| 5,713,917 A | 2/1998 | Leonhardt et al. |
| 5,718,973 A | 2/1998 | Lewis et al. |
| 5,735,892 A | 4/1998 | Myers et al. |
| 5,749,880 A | 5/1998 | Banas et al. |
| 5,800,512 A * | 9/1998 | Lentz et al. ................. 623/1.1 |
| 5,824,050 A | 10/1998 | Karwoski et al. |
| 5,904,967 A | 5/1999 | Ezaki et al. |
| 5,976,192 A | 11/1999 | McIntyre et al. |
| 6,001,125 A | 12/1999 | Golds et al. |
| 6,036,724 A * | 3/2000 | Lentz et al. ................. 623/1.1 |
| 6,080,198 A | 6/2000 | Lentz et al. |
| 6,355,063 B1 * | 3/2002 | Calcote ................... 623/1.42 |
| 6,428,571 B1 * | 8/2002 | Lentz et al. ................. 623/1.4 |
| 6,521,284 B1 * | 2/2003 | Parsons et al. ........... 427/2.24 |
| 6,547,820 B1 * | 4/2003 | Staudenmeier ............ 623/1.49 |

* cited by examiner

PTFE VASCULAR GRAFT AND METHOD OF MANUFACTURE

This application is a of continuation of application Ser. No. 09/525,710, filed on Mar. 14, 2000, now U.S. Pat. No. 6,428,571, which is a continuation-in-part of Ser. No. 09/008/265, filed on Jan. 16, 1998, now U.S. Pat. No. 6,036,724, which is a divisional of Ser. No. 08/588,052, filed on Jan. 22, 1996, now U.S. Pat. No. 5,800,512.

FIELD OF INVENTION

The present invention relates generally to a tubular implantable prosthesis such as vascular grafts and endoprostheses formed of porous polytetrafluoroethylene. More particularly, the present invention relates to a multi-layered tubular self-sealing graft or endoprosthesis formed from primarily expanded polytetrafluoroethylene.

BACKGROUND OF THE INVENTION

It is well known to use extruded tubes of polytetrafluoroethylene (PTFE) as implantable intraluminal prostheses, particularly vascular grafts. PTFE is particularly suitable as an implantable prosthesis as it exhibits superior biocompatability. PTFE tubes may be used as vascular grafts in the replacement or repair of a blood vessel as PTFE exhibits low thrombogenicity. In vascular applications, the grafts are manufactured from expanded polytetrafluoroethylene (ePTFE) tubes. These tubes have a microporous structure which allows natural tissue ingrowth and cell endothelization once implanted in the vascular system. This contributes to long term healing and patency of the graft.

Grafts formed of ePTFE have a fibrous state which is defined by interspaced nodes interconnected by elongated fibrils. The spaces between the node surfaces that is spanned by the fibrils is defined as the internodal distance (IND). A graft having a large IND enhances tissue ingrowth and cell endothelization as the graft is inherently more porous.

The art is replete with examples of microporous ePTFE tubes useful as vascular grafts. The porosity of an ePTFE vascular graft can be controlled by controlling the IND of the microporous structure of the tube. An increase in the IND within a given structure results in enhanced tissue ingrowth as well as cell endothelization along the inner surface thereof However, such increase in the porosity of the tubular structure also results in reducing the overall radial tensile strength of the tube as well as reducing the ability for the graft to retain a suture placed therein during implantation. Also, such microporous tubular structures tend to exhibit low axial tear strength, so that a small tear or nick will tend to propagate along the length of the tube.

The art has seen attempts to increase the radial tensile and axial tear strength of microporous ePTFE tubes. These attempts seek to modify the structure of the extruded PTFE tubing during formation so that the resulting expanded tube has non-longitudinally aligned fibrils, thereby increasing both radial tensile strength as well as axial tear strength. U.S. Pat. No. 4,743,480 shows one attempt to reorient the fibrils of a resultant PTFE tube by modifying the extrusion process of the PTFE tube.

Other attempts to increase the radial tensile, as well as axial tear strength of a microporous ePTFE tube include forming the tubular graft of multiple layers placed over one another. Examples of multi-layered ePTFE tubular structures useful as implantable prostheses are shown in U.S. Pat. Nos. 4,816,338; 4,478,898 and 5,001,276. Other examples of multi-layered structures are shown in Japanese Patent Publication Nos. 6-343,688 and 0-022,792.

Artificial bypass grafts are often used to divert blood flow around damaged regions to restore blood flow. Vascular prostheses may also be used for creating a bypass shunt between an artery and vein. These bypass shunts are often used for multiple needle access, such as is required for hemodialysis treatments. These artificial shunts are preferable to using the body's veins, mainly because veins may either collapse along a puncture track or become aneurysmal, leaky or clotted, causing significant risk of pulmonary embolization.

While it is known to use ePTFE as a vascular prosthesis, and these vascular prostheses have been used for many years for vascular access during hemodialysis, there remain several problems with these implantable ePTFE vascular access grafts. One major drawback in using ePTFE vascular grafts as access shunts for hemodialysis is that because of ePTFE's node-fibril structure, it is difficult to elicit natural occlusion of suture holes in the vascular prosthesis made from ePTFE tubing. As a result, blood cannot typically be withdrawn from an ePTFE vascular graft until the graft has become assimilated with fibrotic tissue. This generally takes 2 to 3 weeks after surgery. Furthermore, ePTFE's propensity for axial tears make it undesirable as a vascular access graft, as punctures, tears, and other attempts to access the blood stream may cause tears which propagate axially with the grain of the node fibril structure.

Providing a suitable vascular access graft has also been attempted in the prior art. Schanzer in U.S. Pat. No. 4,619,641 describes a two-piece coaxial double lumen arteriovenous graft. The Schanzer graft consists of an outer tube positioned over an inner tube, the space between being filled with a self-sealing adhesive. The configuration of this coaxial tube greatly increases the girth of the graft, and limits the flexibility of the lumen which conducts blood flow. Herweck et al., in U.S. Pat. No. 5,192,310 describes a self-sealing vascular graft of unitary construction comprising a primary lumen for blood flow, and a secondary lumen sharing a common sidewall with the primary lumen. A non-biodegradable self-sealing elastomeric material is disposed between the primary and secondary lumen.

While each of the above-referenced patents disclose self-sealing vascular grafts, none disclose a tubular access graft structure exhibiting enhanced radial tensile strength, as well as enhanced resistance to axial tear strength. Furthermore, the multi-layered ePTFE tubular structures and vascular access grafts of the prior art exhibit smaller microporous structure overall, and accordingly a reduction in ability of the graft to promote endothelization along the inner surface. Furthermore, Schanzer does not provide a self-sustaining resealable layer, but rather an elastomeric layer which "fills" the area between the two tubes.

It is therefore desirable to provide a self-sealing ePTFE graft for use in a human body which exhibits increased porosity especially at the inner surface thereof while retaining a high degree of radial strength at the external surface thereof The graft may preferably be used as a vascular access graft.

It is further desirous to produce an ePTFE vascular access graft which exhibits increased porosity at the outer surface thereof while retaining a high degree of radial tensile and suture retention strengths.

It is still further desirous to provide a self-sealing graft with increased resistance to axially propagating tears.

SUMMARY OF THE INVENTION

It is an advantage of the present invention to provide a self-sealing ePTFE graft with increased resistance to axially propagating tears.

It is a further advantage of the present invention to provide a self-sealing ePTFE graft providing superior assimilation capabilities and resealable properties.

It is a further advantage of the present invention to provide a self-sealing ePTFE vascular graft exhibiting an enhanced microporous structure while retaining superior radial strength.

It is a still further advantage of the present invention to provide an ePTFE tubular structure having an inner portion exhibiting enhanced porosity and an outer portion exhibiting enhanced radial tensile strength, suture retention, and suture-hole elongation characteristics.

It is yet another advantage of the present invention to provide a multi-layered ePTFE tubular vascular graft having an inner layer which has a porosity sufficient to promote cell endothelization and an outer layer having a high degree of radial tensile strength.

It is an additional advantage of the present invention to provide a multi-layered ePTFE tubular vascular access graft having an outer layer whose porosity is sufficient to promote enhanced cell growth and tissue incorporation, hence more rapid healing, and an inner layer having a high degree of strength.

In the efficient attainment of these and other advantages, the present invention provides a self-sealing ePTFE graft comprising a first expanded polytetrafluoroethylene (ePTFE) tubular structure having a first porosity, a second ePTFE tubular structure having a second porosity less than said first porosity, said second ePTFE tubular structure being disposed externally about said first ePTFE tubular structure to define a distinct porosity change between said first and second tubular structures, and a resealable polymer layer interposed between said first and second ePTFE tubular structures.

In another embodiment, the present invention provides an ePTFE self-sealing graft, the graft formed of a first ePTFE tubular structure, a second ePTFE tubular structure disposed externally about said first ePTFE tubular structure, and further including a self-sustained resealable polymer layer interposed between the first and second ePTFE tubular structures.

The ePTFE self-sealing graft preferably may be used as a vascular access graft. As more particularly described by way of the preferred embodiment herein, the first and second ePTFE tubular structures are formed of expanded polytetrafluoroethylene (ePTFE). Further, the second ePTFE tubular structure is adheringly supported over the first ePTFE tubular structure to form a composite tubular graft. The strength of this adhesion can be varied as desired to control the characteristics exhibited by the resultant composite structure.

In its method aspect, the present invention provides a method of forming a self-sealing ePTFE graft. The method includes the steps of providing a first ePTFE tubular structure having a desired porosity and strength combination. A second ePTFE tubular structure is provided, also having the desired porosity and strength combination. The second ePTFE structure is disposed over the first ePTFE so as to define a composite vascular graft.

The method of the present invention also provides for the positioning of an intermediate structure between the first and second ePTFE tubular structures. Examples of such structures include an additional ePTFE layer and fibers or thin films of PTFE or other suitable polymers. This intermediate structure also contributes to the resultant porosity and strength of the vascular graft. This intermediate structure can also preferably be a resealable polymer layer interposed between the first and second ePTFE tubular structures.

DETAILED DESCRIPTION OF THE PREFERRED EMBODIMENTS

The prosthesis of the preferred embodiments of the present invention is a multi-layered tubular structure which is particularly suited for use as a vascular access graft. The prosthesis is formed of extruded polytetrafluoroethylene (PTFE) as PTFE exhibits superior biocompatability. In the present invention, a first ePTFE tubular structure having a first porosity is placed circumferentially interior to a second ePTFE tubular structure. Further, a resealable polymer layer is interposed as an intermediate structure between said first and second ePTFE tubular structures.

PTFE is particularly suitable for vascular applications as it exhibits low thrombogenicity. Tubes formed of extruded PTFE may be expanded to form ePTFE tubes where the ePTFE tubes have a fibrous state which is defined by elongate fibrils interconnected by spaced apart nodes. Such tubes are said to have a microporous structure, the porosity of which is determined by the distance between the surfaces of the nodes, referred to as the internodal distance (IND). Tubes having a large IND (greater than 40 microns) generally exhibit long term patency as the larger pores promote cell endothelization along the inner blood contacting surface. Tubes having lower IND (less than 40 microns) exhibit inferior healing characteristics, however they offer superior radial tensile and suture retention strengths desirable in a vascular graft. The present invention provides a composite tubular structure which promotes long term patency of the graft by providing for enhanced cell endothelization along the inner surface while exhibiting enhanced strength due to the presence of the outer layer.

Figure 1:
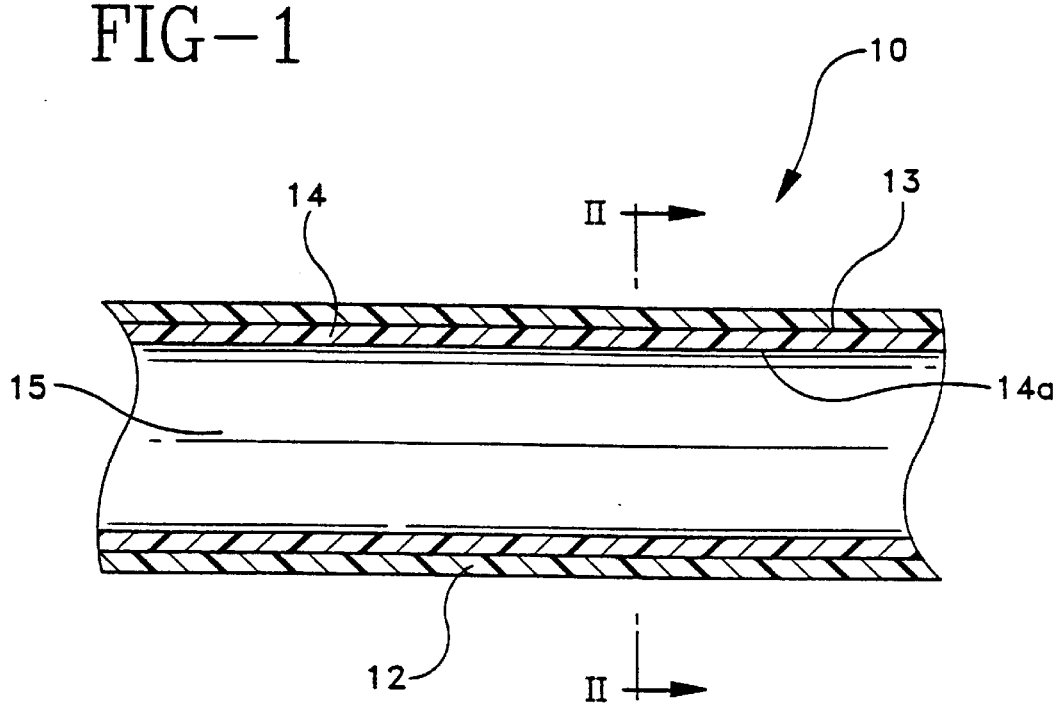
FIG. 1 is a schematic longitudinal cross-section of a multi-layer ePTFE vascular graft of the present invention.
Figure 2:
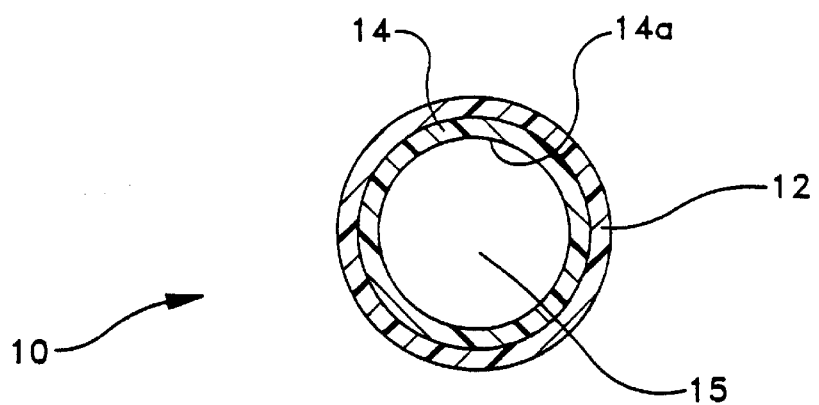
FIG. 2 is a longitudinal cross-section of an alternate embodiment of the present invention producing a multi-layer ePTFE vascular graft.

Referring to FIGS. 1 and 2 of the drawings, composite graft 10 of the present invention is shown. Graft 10 is an elongate tubular structure formed of PTFE. Graft 10 includes a pair of coaxially disposed ePTFE tubes 12 and 14, tube 12 being the outer tube and tube 14 being the inner tube. A central lumen 15 extends through composite graft 10, defined further by the inner wall 14a of inner tube 14, which permits the passage of blood through graft 10 once the graft is properly implanted in the vascular system.

Each tube 12 and 14 may be formed in a separate extrusion process. The process for the paste extrusion of PTFE tubes is well known in the extrusion art. Once extruded, the tubes are expanded to form ePTFE tube. As will be described hereinbelow, the tubes are expanded using differing process parameters (rates, deformation levels, temperatures, etc.) to develop the desired microporous structures. The specifically designed structure of the resulting composite tube has defined properties of strength and porosity which yield a graft 10 having long term patency and good healing characteristics as well as superior strength characteristics. It is also contemplated within the present invention to use PTFE which was extruded as sheets, expanded, and subsequently wrapped to form tubes. An ePTFE tape or ribbon helically wrapped into a tubular structure is also contemplated within the present invention.

The present invention is designed to produce grafts with substantially different node/fibril structures with respect to the internal and external portions of the graft which are adjacent to the internal and external graft surfaces. As an example, the inner tube 14 is designed to have relatively high IND while the outer tube 12 is designed to have a lower IND. Further, a distinct porosity change is clearly defined at the interface 13 between tubes 12 and 14. The inner tube 14 having a higher IND to allow enhanced cell endothelization, while the outer tube 12 having a is lower IND provides superior strength to the overall composite.

Figure 3:
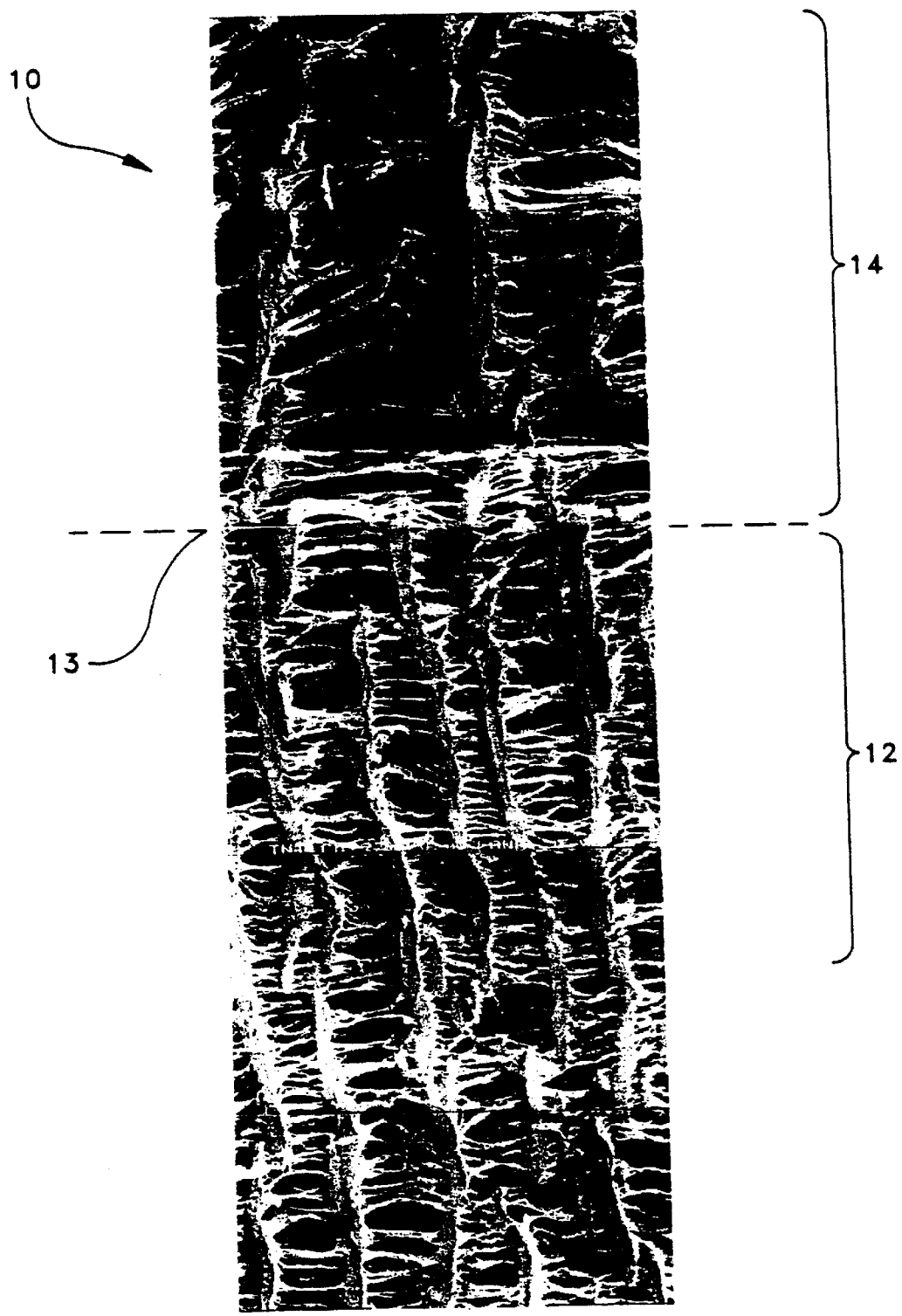
FIG. 3 is a scanning electron micrograph showing a cross-sectional view of a vascular graft produced using the present invention.

An electron micro graph of such a structure produced according to the present invention is shown in FIG. 3. The disparate IND's between the inner tube 14 and outer tube 12 are clearly evident, along with the step change in IND at the interface 13 between the inner tube 14 and outer tube 12. In this example, the strength of the interface 13 has been established by the processing conditions described below to fully adhere the inner tube 14 and outer tube together, hence preventing relative motion and providing enhanced strength.

Graft 10 of the present invention may be formed by expanding a thin wall inner tube 14 at a relatively high degree of elongation, on the order of approximately between 400 and 2000% elongation preferably from about between 700% and 900%. Tube 14 is expanded over a cylindrical mandrel (not shown), such as a stainless steel mandrel at a temperature of between room temperature and 645° F., preferably about 500° F. Tube 14 is preferably but not necessarily fully sintered after expansion. Sintering is typically accomplished at a temperature of between 645° F. and 800° F. preferably at about 660° F. and for a time of between about 5 minutes to 30 minutes, preferably about 15 minutes. The combination of the ePTFE tube 14 over the mandrel is then employed as a second mandrel, over which outer tube 12 is expanded. The ID of the outer tube 12 is selected so that it may be easily but tightly disposed over the OD of inner tube 14. The composite structure 10 is then sintered at preferably similar parameters. The level of elongation of outer tube 12 is lower than that of inner tube 14, approximately between 200% and 500% elongation preferably about 400%. The expansion and sintering of outer tube 12 over the inner tube 14 serves to adheringly bond the interface 13 between the two tubes, resulting in a single composite structure 10.

In an alternate embodiment the outer tube ID may be less than the inner tube OD. In this embodiment, the outer tube is thermally or mechanically radially dilated to fit over the inner tube. The composite structure may then be sintered at about 660° F. Construction in this manner provides a snug fit of the tubes, and enhances the bonding interface between tubes, and also may augment recoil properties of an elastomeric intermediate layer.

As shown in FIG. 3, the resulting composite structure has an inner surface defined by inner tube 14 which exhibits an IND of between 40 and 100 microns, spanned by a moderate number of fibrils. Such microporous structure is sufficiently large so as to promote enhanced cell-endothelization once blood flow is established through graft 10. Such cell-endothelization enhances the long term patency of the graft.

The outer structure, defined by outer tube 12, has a smaller microporous structure, with IND of about 15–35 microns and a substantial fibril density. Such outer structure results in an increase in the strength of the outer tube, and hence of the composite structure. Importantly, the outer surface defined by the outer tube 12 exhibits enhanced suture retention due to the smaller IND.

Furthermore, the resulting composite structure exhibits a sharp porosity change between the outer tube 12 and inner tube 14. This sharp porosity transition is achieved by providing an inner tube 14 having generally a given uniform porosity therealong and then providing a separate outer tube 14 having a resultant different porosity uniformly thereal-ong. Thus a distinct porosity change is exhibited on either side of the interface 13 defined between inner tube 14 and outer tube 12.

In addition, the forming process described above results in a bonded interface between the inner tube 14 and outer tube 12. The interface exhibits sufficient interfacial strength resulting from the direct sintering of the outer tube 12 over inner tube 14 so as to assure complete bonding of the two tubes. The strength of the interface between the two tubes may be independently varied through selection of processing conditions and relative dimensions of precursor extruded tubes 12 and 14 as desired to yield a range of performance.

Figure 4:
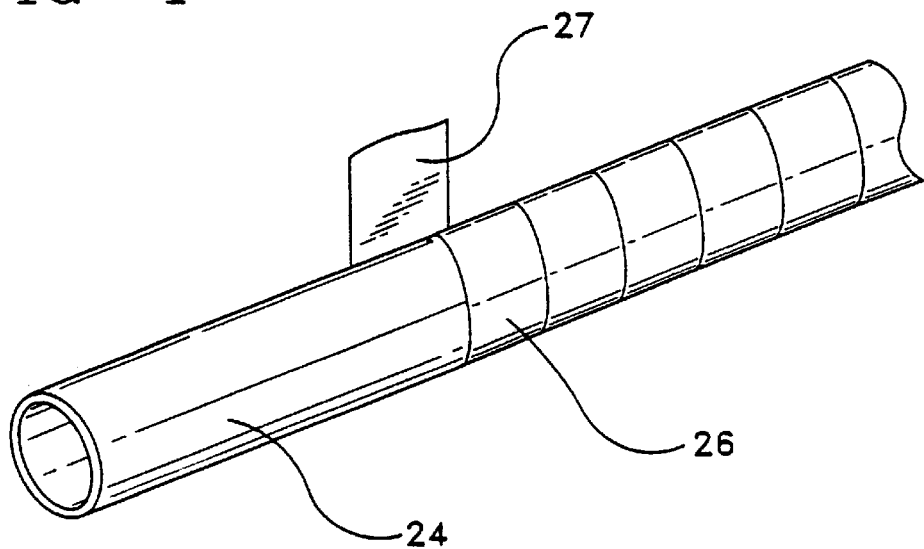
FIG. 4 is a perspective showing of one of the tubular structures of the graft of FIG. 1 over-wrapped with a layer of ePTFE tape.
Figure 5:
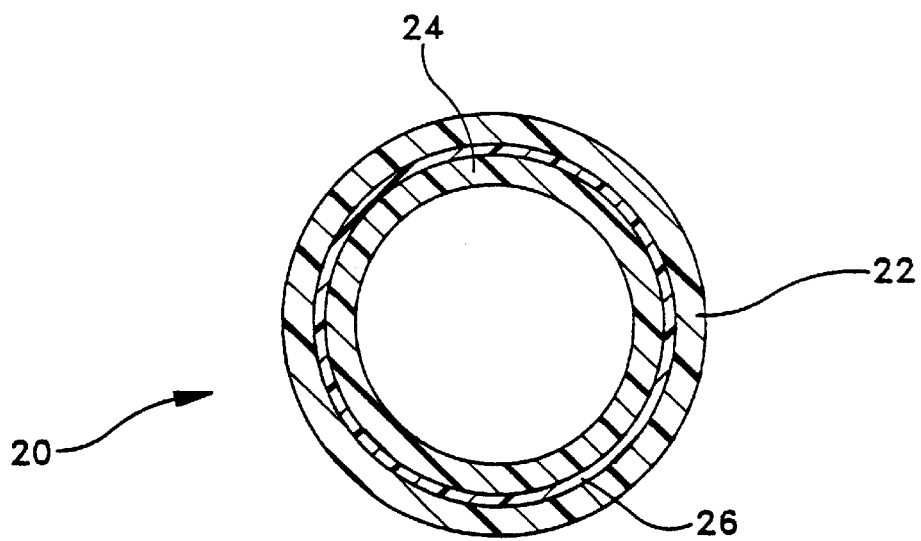
FIG. 5 is a cross-sectional showing of an alternate embodiment of the ePTFE vascular graft of the present invention.

Referring now to FIGS. 4 and 5, a further embodiment of the present invention is shown. Tubular graft 20 is a composite structure similar to graft 10 described above. Graft 20 includes an outer tube 22 and an inner tube 24 formed generally in the manner described above. In order to further control the porosity and strength of the graft 20, especially at the interface between outer tube 22 and inner tube 24, an additional layer may be employed in combination with outer tube 22 and inner tube 24.

As specifically shown in FIGS. 4 and 5, an additional layer 26 may be employed between inner tube 24 and outer tube 22. Layer 26 may include a helical wrap of ePTFE tape 27 placed over inner tube 24. The additional layer 26, however, may also exist as a sheet, film, yarn, monofilament or multi filament wrap, or additional tube. The additional layer 26 may consist of PTFE, FEP, or other suitable polymer composition to obtain the desired performance characteristics. Layer 26 may be used to impart enhanced properties of porosity and/or strength to the composite graft 20. For example, an additional layer 26 of ePTFE tape 27 having a low IND and wrapped orthogonally to the length direction of graft 20 would increase the radial strength of the resultant composite graft. Similarly, a layer of ePTFE having a high IND would increase the porosity of the composite structure thereby further promoting cell endothelization and/or tissue ingrowth.

In a preferred embodiment of the present invention, the intermediate layer may be a resealable polymer layer, employed in order to create a self-sealing graft. The self-sealing graft may be preferably used as a vascular access device. The graft is also preferably implantable. When used as an access device, the graft allows repeated access to the blood stream through punctures, which close after removal of the penetrating member (such as, e.g., a hypodermic needle or cannula) which provided the access.

The intermediate, or resealable polymer layer may be additionally augmented with a pre-sintered PTFE (or FEP)

bead wrap, or wire support coil. The pre-sintered PTFE bead wrap is a cylindrically extruded solid tube of PTFE that is sintered, then helically wrapped around the desired layer (inner, intermediate, or outer). A graft of this embodiment shows enhanced strength and handling characteristics, i.e., crush resistance, kink resistance, etc.

In another preferred embodiment, a self-sustained resealable polymer layer may be interposed between first and second ePTFE tubular structures. For the purpose of this specification, the term self-sustained refers to a tubular structure which possesses enough structural stability to be formed and subsequently stand alone without the use of additional tubular layers, or any other "molding" type formation, i.e., not a resinous polymer which is injected, or fills a space between an outer and inner tube. Some examples include the elastomeric layers employed in the present invention, as well as the resealable intermediate layers shown in Examples 3 and 4 of the present invention.

The ePTFE self-sealing graft can be used for any medical technique in which repeated hemoaccess is required, for example, but without intending to limit the possible applications, intravenous drug administration, chronic insulin injections, chemotherapy, frequent blood samples, connection to artificial lungs, and hyperalimentation. The self-sealing ePTFE graft is ideally suited for use in chronic hemodialysis access, e.g., in a looped forearm graft fistula, straight forearm graft fistula, an axillary graft fistula, or any other AV fistula application. The self-sealing capabilities of the graft are preferred to provide a graft with greater suture retention, and also to prevent excessive bleeding from a graft after puncture (whether in venous access or otherwise).

The graft is made self-sealing with the use of a resealable polymer layer interposed between said first and second polymer layer. The resealable layer functions by primarily two different mechanisms. In one embodiment, the resealable polymer layer comprises an elastomeric component. The term elastomeric as used herein refers to a substance which is capable of essentially rebounding to near its initial form or state after deformation. In another embodiment, the resealable polymer layer comprises a flowable material layer. The term flowable as used herein refers to an amorphous material which fills a void created by a deformation or puncture.

It is further contemplated within the present invention to provide a composite vascular graft with an intermediate resealable layer, and multiple interior or exterior layers of ePTFE. Furthermore, the use of multiple intermediate layers possessing resealable properties is also contemplated within the present invention.

A number of different materials may be employed to provide an elastomeric polymer component as contemplated in the present invention. Furthermore, the elastomeric properties of the intermediate layer may be imparted thereto as a result of an inherent property of the material used, or as a result of the particular method of constructing such a layer. The elastomeric component may also be adhered to the first and second ePTFE tubular structures. The adhesion may take place by mechanical means, chemical means (use of an adhesive), either, or both. Some polymers, particularly thermoplastic elastomers, become sufficiently tacky through heating to adhere to the ePTFE tubular structures. The elastomeric component may also exert a force in the direction of the puncture, which if adhered to the first and/or second ePTFE tubular structures may provide for either layer to seal the puncture site. Some materials which may be used as an elastomeric component in various forms include, but are not limited to, polymers and copolymers, including thermoplastic elastomers and certain silicones, silicone rubbers, synthetic rubbers, polyurethanes, polyethers, polyesters, polyamides and various fluoropolymers, including, but not limited to PTFE, ePTFE, FEP (fluorinated ethylene propylene copolymer), and PFA (polyfluorinated alkanoate). The materials may be utilized as the elastomeric polymer layer in a number of different forms which would impart the desired elastomeric characteristics to the layer. In one embodiment, an extruded polymeric ribbon or tape wrap may be wrapped helically into a tubular shape under tension. Alternatively, a sheet, fiber, thread, or yarn may also be wrapped under tension to impart an elastomeric layer.

In another preferred embodiment, a polymeric layer may be applied from solution. The polymer may be dissolved or partially dissolved in a solvent, and upon evaporation of the solvent, the polymer is deposited as an elastomeric layer. The solvents used in this system must be capable of wetting the ePTFE tubular surfaces. Upon evaporation of the solvent, an elastomeric layer is deposited which may penetrate into the pores of the adjacent ePTFE layer to provide an anchoring effect for the polymeric layer. Upon evaporation of the solvent, the elastomeric layer may also shrink to provide the desired elastomeric characteristics.

In another embodiment of the elastomeric layer of the present invention, a solvent spun polyurethane as disclosed in U.S. Pat. Nos. 4,810,749; 4,738,740; 4,743,252 and 5,229,431, herein incorporated by reference, may be employed. From such elastomeric fibers may be formed a woven or non-woven textile-like layer with sufficient fiber density to form a sealing layer while allowing a puncturing member such as a hypodermic needle or cannula to penetrate between the individual fibers. Furthermore, the elastomeric fibers of said textile-like structure may be employed under tension or compression to facilitate the recovery of the fibers displaced by the penetrating member to their original position after removal by the penetrating member.

Furthermore the elastomeric layer of the present invention may additionally be impregnated with a gel to provide enhanced sealing capabilities. Examples of such gels are hydrogels formed from natural materials including, but not limited to, gelatin, collagen, albumin, casein, algin, carboxy methyl cellulose, carageenan, furcellaran, agarose, guar, locust bean gum, gum arabic, hydroxyethyl cellulose, hydroxypropyl cellulose, methyl cellulose, hydroxyalkylmethyl cellulose, pectin, partially deacetylated chitosan, starch and starch derivatives, including amylose and amylopectin, xanthan, polylysine, hyaluronic acid, and its derivatives, heparin, their salts, and mixtures thereof A number of different flowable polymer layers may be interposed between said first and second tubular structures to provide a self-sealing graft. The flowable polymer layer seals the graft by possessing an amorphous quality which fills in any space left open subsequent to puncture of the graft. It may simply fill in the space left open in the interposed middle layer, or it may additionally penetrate into the first and/or second ePTFE tubular structures to fill any void left form puncture of either layer.

An example of a flowable polymer which may be used in the present invention is an uncured or partially cured polymer. The polymer may be cured by a number of activating means which would activate curing subsequent to puncture of the graft, thereby sealing with the curing of the polymer. Examples of materials for such a flowable layer include, but are not limited to, uncured elastomers such as natural or synthetic rubbers, and natural gums such as gum arabic.

Materials that are particularly useful in a flowable layer include non-crosslinked polyisobutylene which is also known as uncured butyl rubber.

Another flowable polymer layer which may be employed in the present invention a gel. Gels are generally suspensions or emulsions of polymers which have properties intermediate the liquid and solid states. A hydrogel may also be used in the present invention, and refers to polymeric material which swells in water without dissolving, and which retains a significant amount of water in its structure. The gels and hydrogels employed in the present invention may be biodegradable, or non-biodegradable. They also further may have polymeric beads (not to be confused with the pre-sintered PTFE bead-wrap, which imparts structural stability) suspended within the gel to effectuate sealing of the prosthesis. Some examples of gels which may be used in the present invention include, but are not limited to, silicone gels, gum arabic, and low molecular weight ethylene/vinyl acetate polymers.

The following examples serve to provide further appreciation of the invention but are not meant in any way to restrict the scope of the invention.

EXAMPLE I

A thin extruded tube having wall thickness of 0.41 mm and an inner diameter of 6.2 mm was expanded over a stainless steel mandrel at 500° F. to 900% elongation. The ePTFE tube was then sintered at 660° F. for 14 minutes, cooled, and removed from the oven. A second thin extruded tube having wall thickness of 0.45 mm and an inner diameter of 6.9 mm was expanded over the first tube/mandrel combination at 500° F. and 400% elongation. The composite was then sintered at 660° F. for 14 minutes, cooled and removed from the oven. The resultant composite tube had a wall thickness of 0.65 mm and ID of 5.8 mm.

EXAMPLE 2

A thin extruded tube having wall thickness of 0.41 mm and an inner diameter of 6.2 mm was expanded over a stainless steel mandrel at 500° F. to 700% elongation. The ePTFE tube was then sintered at 660° F. for 14 minutes, cooled, and removed from the oven. A second thin extruded tube having wall thickness of 0.45 mm and an inner diameter of 6.9 mm was expanded over the first tube at 500° F. and 400% elongation. The composite was sintered at 660° F. for 14 minutes, cooled, and removed from the oven. The resultant composite tube had a wall thickness of 0.67 mm and an inner diameter of 5.8 mm.

Table I presents physical property data for a vascular graft of the type depicted in Example I described above. The composite graft was removed from the mandrel and subjected to standard testing of radial tensile strength and suture hole elongation. The radial strength of the 900%/400% composite graft is equivalent to a single layer 400% elongation graft and substantially stronger than a single layer 900% elongation graft, despite an overall thinner wall dimension. Additionally, the superior strength of the composite graft is demonstrated by the higher elongation capable of being borne by the graft prior to failure. The lower suture hole elongation, indicative of a smaller tear being caused by suturing and tensioning at a fixed value of 100 grams is clearly demonstrated for the graft prepared by the method of the current invention.

TABLE 1

| Physical Property Measurement | 400% Elongation Single Layer Graft | 900%/400% Elongation Composite Graft | 900% Elongation Single Layer Graft |
|---|---|---|---|
| Radial Tensile Strength ($kg/mm^2$) | 0.48 | 0.48 | 0.2 |
| Radial Strain at Break (%) | 550 | 690 | 531 |
| Suture Hole Elongation (%) | 87 | 81 | 158 |
| Wall Thickness | 0.72 | 0.65 | 0.73 |

EXAMPLE 3

Three composite grafts were constructed and their ability to reseal after a puncture was tested. Graft No. 1 is an ePTFE helically tape-wrapped graft with no resealable layer, and graft Nos. two (2) and three (3) were constructed with a resealable intermediate layer in the below-described procedure.

Graft No. 1 is an ePTFE graft used as the control in the following experiment. Graft 2 was constructed by first placing an ePTFE tubular structure with an inner diameter of 5 millimeters on a mandrel. A thermoplastic elastomer tubing was then slid over the ePTFE tube. Because of the tackiness of the thermoplastic elastomeric tubing, it was necessary to manipulate the tubing by rolling and stretching it in order to maneuver it over the first ePTFE tubular structure to lie evenly thereon. A second ePTFE tubular structure with an inner diameter of five (5) millimeters was then radially stretched, or expanded to yield an ePTFE tubular structure with an inner diameter of 8 millimeters. A metal sleeve was then placed over the thermoplastic elastomer-covered tubular structure. The second 8 mm inner diameter ePTFE tubular structure was then placed onto the metal sleeve. The metal sleeve was then retracted allowing the second tubular structure to come into contact with the thermoplastic elastomer.

Both grafts Nos. 2 and 3 were prepared using this procedure. Graft 2 was then placed in an oven and heated at 350° F. for 10 minutes. There appeared to be little bonding between the layers, and the graft was then heated for an additional 10 minutes at 450° F.

Graft 3 was heated for five minutes at 400° F. The material did not appear to bond together, so the graft was then heated at 425° F. for an additional five minutes.

Grafts Nos. 1–3 were then tested for quality control. Each graft was placed in a water entry pressure measuring device to provide a constant pressure of water within the graft. The water pressure was maintained at three pounds per square inch. The grafts were then punctured with a 20 gauge needle. The needle was then removed and any water leaving the puncture site was collected in a beaker and measured over the time of collection. This procedure was followed for a number of test runs. The results are shown in table two below.

TABLE 2

| Run Number | Graft No. 1 (grams water/ 30 seconds) | Graft No. 2 (grams water/ 30 seconds) | Graft No. 3 (grams water/ 30 seconds) |
|---|---|---|---|
| 1 | 21.7 | 0.2 | 1.2 |
| 2 | 20.0 | 1.3 | 0.5 |
| 3 | 23.1 | 0.2 | — |

TABLE 2-continued

| Run Number | Graft No. 1 (grams water/ 30 seconds) | Graft No. 2 (grams water/ 30 seconds) | Graft No. 3 (grams water/ 30 seconds) |
|---|---|---|---|
| 4 | 20.0 | 1.4 | — |
| 5 | 21.9 | — | — |
| Average Of Trial Runs | 21.34 | 0.775 | 0.85 |

Graft No. 1 leaked steadily, as the puncture did not reseal. While graft numbers 2 and 3 showed minimal leakage. In both cases, the water leaked in a small trickle in the first few seconds (2–5 seconds), then stopped or slowed to an immeasurable seepage.

EXAMPLE 4

Three additional grafts were constructed with an intermediate resealable layer and tested determine their ability to seal after puncture.

Graft No.4 was made using an ePTFE graft with an initial 5 millimeter inner diameter as the inner tubular structure. The 5 mm ePTFE tube was extruded using a die insert of 0.257 inches, and a mandrel of 0.226 inches. The inner tube was then stretched longitudinally to 500% its original length, and sintered. The inner tube was then stretched radially by placing it on a 5.95 mm mandrel. A pre-sintered PTFE bead-wrap (0.014 inch±0.002 inch diameter, length approximately 30 cm) was then helically wrapped around the exterior of the inner tube at 650 revolutions per minute (RPM), and with a mandrel speed traversely at 800 RPMs. The wrap helically repeated on the tube at approximately every 3.5 cm, and at an angle of approximately 10°–50° with respect to a radial axis. After wrapping, the coil wrapped tube was then heated in an oven at 663° F. for 10 minutes to sinter the beads to the grafts.

A second ePTFE tube was then added exterior the beaded coil and inner tube. The second ePTFE tube also had a 5 millimeter inner diameter, and was a tube extruded using a die insert of 0.271 inches and mandrel size 0.257 inches, and was stretched to longitudinally 500% its original length and sintered. The second ePTFE tube was then radially stretched over a tapered 6–10 mm mandrel to a graft of inner diameter of 10 mms. The second graft was then transferred to a 10 mm hollow mandrel within which the inner bead-wrapped graft was placed. The hollow mandrel was then slid out to leave the second ePTFE tube exteriorly placed on the bead covered graft. The composite device was then placed in an oven for 20 minutes and heated at 663° F. Three 3 cm long tubular rings of thermoplastic elastomer (C-FLEX®) were then placed over the composite stent graft. The rings had an inner diameter of 6.5 mms. A third outer ePTFE tubular structure was then placed over the C-FLEX rings. The third outer tubular structure was a 3 mm inner diameter ePTFE extruded tube was made using a die insert of 0.189 inches, and was stretched longitudinally to 700% its original length and sintered. The third outer structure was then expanded radially by stretching the tube over a 4–7 mm continuously tapered mandrel, then further radially expanded over a 6–10 mm continuously tapered mandrel. It was then placed on a 10 mm hollow mandrel with the C-FLEX covered composite graft placed within the mandrel, and the outer tube then covers the C-FLEX® upon removal of the hollow mandrel. Graft 4 was then heated for 5 minutes at 435° F.

Graft No. 5 was constructed using a 5 mm inner diameter ePTFE extruded tube as the inner tubular structure. The 5 mm tube was then radially stretched over a 5.95 mm diameter mandrel. A corethane intermediate layer was then spun into a tube of 6 mm diameter with 250 passes, and subsequently loaded onto the inner ePTFE tube. A second outer ePTFE tubular structure (originally a 5 mm inner diameter) was then stretched to 10 mm over a 6–10 mm continuously tapered mandrel. Graft No. 5 was then heated for 15 minutes at 400° F.

Graft No. 6 was made using a 5 mm inner diameter ePTFE graft as the inner tubular structure. The inner tube was then stretched over a 6.2 mm hollow expansion mandrel. An ePTFE yarn was then wrapped in two helical directions over the inner tube. A corethane layer was then spun over the yarn wrapping as the third tubular layer at a mandrel speed of 1,000 RPMs and a wrap angle of 50 degrees. The corethane covered graft was then heated at 230° F. for 10 minutes. An outer ePTFE tube with a 5 mm inner diameter was then stretched to 10 mm over a 6–10 mm continuously tapered mandrel. It was then mounted on the corethane layer with the use of the hollow mandrel. Graft 6 was then heated for 30 minutes at 340° F.

Grafts 4–6 were all tested by puncturing them with a constant pressure water source attached to them as done with Grafts Nos. 1–3. The results are shown in Table 3 below.

TABLE 3

| Run No. | Graft 4 (grams water/ seconds) | Graft 5 (grams water/ seconds) | Graft 6 (grams water/ seconds) |
|---|---|---|---|
| 1 | 0.2 | 0 | 0 |
| 2 | 0 | 0 | 0 |
| 3 | 0 | 0.7 | 0 |

Various changes to the foregoing described and shown structures would now be evident to those skilled in the art. Accordingly, the particularly disclosed scope of the invention is set forth in the following claims.

What is claimed is:

1. A multi-layered ePTFE graft comprising:
   a first ePTFE tubular structure having a first porosity;
   a second ePTFE tubular structure having a different porosity than said first porosity, said second ePTFE tubular structure being disposed externally about said first ePTFE tubular structure; and
   a self-sealing material interposed between said first and second ePTFE tubular structures,
   wherein said self-sealing material is selected from the group consisting of sheet, film, yarn, thread, mono-filament wrap, multi-filament wrap, tube, solvent-spun elastomeric fibers, helically-wound tape, and combinations thereof.

2. A multi-layered graft according to claim 1 wherein said first porosity is greater than said second porosity.

3. A multi-layered graft according to claim 1 wherein said self-sealing material is selected from the group consisting of thermoplastic elastomers, silicones, silicone rubbers, synthetic rubbers, polyurethanes, polyethers, polyesters, polyamides, fluoropolymers and combinations thereof.

4. A multi-layered graft according to claim 1 wherein said self-sealing material comprises a single layer having resealable properties.

5. A multi-layered graft according to claim 1 wherein said self-sealing material comprises an elastomeric polymer layer.

6. A multi-layered graft according to claim 5 wherein said self-sealing elastomeric polymer layer adheres to said first and second ePTFE tubular structures.

7. A multi-layered graft according to claim 6, wherein said adherence is by chemical means, mechanical means or a combination thereof.

8. A multi-layered graft according to claim 5 wherein said elastomeric polymer layer comprises an internodal distance sufficient to promote cell endothelization and/or tissue ingrowth.

9. A multi-layered graft according to claim 5 wherein said elastomeric polymer layer comprises an internodal distance sufficient to promote enhanced strength and handling characteristics of the graft.

10. A multi-layered graft according to claim 5 wherein said elastomeric polymer layer is impregnated with a gel to enhance sealing properties thereof.

11. A multi-layered graft according to claim 1 wherein said solvent-spun elastomeric fibers form a woven or non-woven layer.

12. A multi-layered graft according to claim 1 wherein said solvent-spun elastomeric fibers have sufficient fiber density to form a sealing layer while allowing a puncturing member to penetrate between said solvent-spun elastomeric fibers.

13. A multi-layered graft according to claim 1 wherein said solvent-spun elastomeric fibers comprise solvent-spun polyurethane.

14. A multi-layered graft according to claim 1 wherein said self-sealing material is flowable.

15. A multi-layered ePTFE graft comprising:
   a first ePTFE tubular structure having a first porosity;
   a second ePTFE tubular structure having a different porosity than said first porosity, said second ePTFE tubular structure being disposed externally about said first ePTFE tubular structure; and
   a self-sealing material interposed between said first and second ePTFE tubular structures,
wherein said self-sealing material comprises multiple layers having resealable properties.

16. A multi-layered ePTFE graft comprising:
   a first ePTFE tubular structure having a first porosity;
   a second ePTFE tubular structure having a different porosity than said first porosity, said second ePTFE tubular structure being disposed externally about said first ePTFE tubular structure; and
   a self-sealing material interposed between said first and second ePTFE tubular structures,
wherein said self-sealing material is augmented with a pre-sintered fluoropolymer bead wrap.

17. A multi-layered ePTFE graft comprising:
   a first ePTFE tubular structure having a first porosity;
   a second ePTFE tubular structure having a different porosity than said first porosity, said second ePTFE tubular structure being disposed externally about said first ePTFE tubular structure; and
   a self-sealing material interposed between said first and second ePTFE tubular structures,
wherein said self-sealing material is augmented with a wire support coil.

18. A multi-layered ePTFE graft comprising:
   a first ePTFE tubular structure having a first porosity;
   a second ePTFE tubular structure having a different porosity than said first porosity, said second ePTFE tubular structure being disposed externally about said first ePTFE tubular structure; and
   a self-sealing material interposed between said first and second ePTFE tubular structures,
wherein said self-sealing material is a self-sustained tubular structure.

19. A multi-layered graft according to claim 18 wherein said self-sustained tubular structure is a thermoplastic elastomer tube or a fluoropolymer tube.

20. A multi-layered ePTFE vascular graft useful for repeated hemoaccess comprising:
   a first ePTFE tubular structure having a first porosity;
   a second ePTFE tubular structure having a different porosity than said first porosity, said second ePTFE tubular structure being disposed externally about said first ePTFE tubular structure; and
   a self-sealing material interposed between said first and second ePTFE tubular structures,
wherein said self-sealing material is selected from the group consisting of sheet, film, yarn, thread, mono-filament wrap, multi-filament wrap, tube, solvent-spun elastomeric fibers, helically-wound tape, and combinations thereof.

21. A multi-layered graft according to claim 20 wherein said first porosity is greater than said second porosity.

22. A multi-layered ePTFE vascular graft useful for repeated hemoaccess comprising:
   a first ePTFE tubular structure having a first porosity;
   a second ePTFE tubular structure having a different porosity than said first porosity, said second ePTFE tubular structure being disposed externally about said first ePTFE tubular structure; and
   a self-sealing material interposed between said first and second ePTFE tubular structures,
wherein said self-sealing material is selected from the group consisting of thermoplastic elastomers, silicones, silicone rubbers, synthetic rubbers, polyurethanes, polyethers, polyesters, polyamides, fluoropolymers and combinations thereof.

23. A multi-layered ePTFE vascular graft useful for repeated hemoaccess comprising:
   a first ePTFE tubular structure having a first porosity;
   a second ePTFE tubular structure having a different porosity than said first porosity, said second ePTFE tubular structure being disposed externally about said first ePTFE tubular structure; and
   a self-sealing material interposed between said first and second ePTFE tubular structures,
wherein said self-sealing material is a self-sustained tubular structure.

24. A multi-layered graft according to claim 23 wherein said self-sealing material comprises a single layer having resealable properties.

25. A multi-layered ePTFE vascular graft useful for repeated hemoaccess comprising:
   a first ePTFE tubular structure having a first porosity;
   a second ePTFE tubular structure having a different porosity than said first porosity, said second ePTFE tubular structure being disposed externally about said first ePTFE tubular structure; and
   a self-sealing material interposed between said first and second ePTFE tubular structures,
wherein said self-sealing material comprises multiple layers having resealable properties.

* * * * *

UNITED STATES PATENT AND TRADEMARK OFFICE
CERTIFICATE OF CORRECTION

PATENT NO. : 6,719,783 B2
DATED : April 13, 2004
INVENTOR(S) : David Lentz et al.

It is certified that error appears in the above-identified patent and that said Letters Patent is hereby corrected as shown below:

Column 1,
Line 44, delete "...surface thereof However, such.." and insert -- ...surface thereof. However, such... --.

Column 2,
Line 59, delete "...thereof The graft may.." and insert -- ...thereof. The graft may... --.

Column 5,
Line 23, delete "...tube 12 having a is lower IND..." and insert -- ...tube 12 having a lower IND... --.

Column 8,
Line 50, delete "...and mixtures thereof..." and insert -- ...and mixtures thereof. ... --.
Line 59, delete "...left form puncture of either..." and insert -- ..left from puncture of either... --.

Column 9,
Line 6, delete "...present invention a gel. Gels..." and insert -- ...present invention is a gel. Gels... --.

Column 11,
Lines 11-12, delete "...did not reseal. While graft..." and insert -- ...did not reseal, while graft... --.
Line 19, delete "...and tested determine their..." and insert -- ...and tested to determine their... --.
Lines 55-56, delete "...structure was a 3 mm inner diameter e PTFE extruded tube was made using..." and insert -- ...structure, a 3 mm inner diameter ePTFE extruded tube, was made using... --.

UNITED STATES PATENT AND TRADEMARK OFFICE
CERTIFICATE OF CORRECTION

PATENT NO. : 6,719,783 B2
DATED : April 13, 2004
INVENTOR(S) : David Lentz et al.

It is certified that error appears in the above-identified patent and that said Letters Patent is hereby corrected as shown below:

Column 13,
Line 5, delete "...an intemodal distance..." and insert -- ...an internodal distance... --.

Signed and Sealed this

Tenth Day of August, 2004

JON W. DUDAS
*Acting Director of the United States Patent and Trademark Office*